United States Patent
Tamura

(10) Patent No.: US 11,880,029 B2
(45) Date of Patent: Jan. 23, 2024

(54) ENDOSCOPE AND ENDOSCOPE SYSTEM FOR CONTROLLING AMOUNT OF ILLUMINATION LIGHT OF LIGHT SOURCE

(71) Applicant: OLYMPUS CORPORATION, Tokyo (JP)

(72) Inventor: Kazuaki Tamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 522 days.

(21) Appl. No.: 17/123,356

(22) Filed: Dec. 16, 2020

(65) Prior Publication Data

US 2021/0137373 A1  May 13, 2021

Related U.S. Application Data

(63) Continuation of application No. PCT/JP2018/024337, filed on Jun. 27, 2018.

(51) Int. Cl.
*G02B 23/24* (2006.01)
*A61B 1/06* (2006.01)
(Continued)

(52) U.S. Cl.
CPC ...... *G02B 23/2469* (2013.01); *A61B 1/00006* (2013.01); *A61B 1/044* (2022.02);
(Continued)

(58) Field of Classification Search
None
See application file for complete search history.

(56) References Cited

U.S. PATENT DOCUMENTS

| 4,695,714 A * | 9/1987 | Kimizuka ........... H01S 5/02453 |
| | | 250/238 |
| 2003/0050534 A1 * | 3/2003 | Kazakevich ......... A61B 1/0607 |
| | | 600/179 |

(Continued)

FOREIGN PATENT DOCUMENTS

| EP | 2 415 390 A1 | 2/2012 |
| JP | 2010-142288 A | 7/2010 |

(Continued)

OTHER PUBLICATIONS

International Search Report dated Aug. 7, 2018 received in JP2018/024337.

*Primary Examiner* — John P Leubecker
(74) *Attorney, Agent, or Firm* — Scully, Scott, Murphy & Presser, P.C.

(57) ABSTRACT

The endoscope system includes: a laser diode for an endoscope that emits illumination light whose amount can be controlled; an image pickup device that outputs an image pickup signal of an image obtained by receiving reflected light of the illumination light; a photodiode that receives a part of the illumination light of the laser diode; a thermistor that detects a temperature of the laser diode; a thermistor that detects a temperature of the photodiode; a detection light amount temperature correction circuit that corrects an amount of light received by the photodiode based on the temperature of the photodiode; and a laser diode control circuit that controls driving of the laser diode so that an amount of the illumination light becomes a set value based on a corrected amount of received light corrected by the detection light amount temperature correction circuit and the temperature of the laser diode.

12 Claims, 11 Drawing Sheets

(51) Int. Cl.
*A61B 1/07* (2006.01)
*H01S 5/00* (2006.01)
*A61B 1/00* (2006.01)
*H01S 5/068* (2006.01)
*A61B 1/04* (2006.01)

(52) U.S. Cl.
CPC .......... *A61B 1/0638* (2013.01); *A61B 1/0653* (2013.01); *A61B 1/0655* (2022.02); *A61B 1/07* (2013.01); *G02B 23/2484* (2013.01); *H01S 5/0087* (2021.01); *H01S 5/06804* (2013.01)

(56) References Cited

U.S. PATENT DOCUMENTS

| | | | | |
|---|---|---|---|---|
| 2004/0042065 | A1* | 3/2004 | Nakaji | H04B 10/296 |
| | | | | 359/341.41 |
| 2007/0040512 | A1* | 2/2007 | Jungwirth | H05B 45/22 |
| | | | | 315/159 |
| 2008/0215279 | A1* | 9/2008 | Salsbury | H05B 45/28 |
| | | | | 702/107 |
| 2009/0251684 | A1* | 10/2009 | Arai | H01S 5/06804 |
| | | | | 356/43 |
| 2011/0193948 | A1* | 8/2011 | Amling | A61B 1/00029 |
| | | | | 348/E7.085 |
| 2012/0025715 | A1* | 2/2012 | Picciotto | H05B 45/28 |
| | | | | 362/235 |
| 2012/0035419 | A1 | 2/2012 | Ashida et al. | |
| 2015/0146751 | A1* | 5/2015 | Downing | A62D 3/00 |
| | | | | 315/158 |
| 2017/0202445 | A1* | 7/2017 | Sakai | G02B 23/2469 |
| 2017/0283760 | A1* | 10/2017 | Peng | C12M 41/42 |
| 2018/0136454 | A1* | 5/2018 | Yoshida | G02B 23/2469 |
| 2019/0097396 | A1* | 3/2019 | Sakai | G02B 26/0833 |

FOREIGN PATENT DOCUMENTS

| | | | | |
|---|---|---|---|---|
| JP | 2010-253090 A | 11/2010 | | |
| JP | 2012-030004 A | 2/2012 | | |
| JP | 2012-034950 A | 2/2012 | | |
| JP | 2012-094891 A | 5/2012 | | |
| JP | 2017158634 A * | 9/2017 | ......... | A61B 1/00172 |
| JP | 2017-207412 A | 11/2017 | | |

* cited by examiner

FIG. 7

TBL1

|  |  | DRIVING CONDITION | | | |
|---|---|---|---|---|---|
|  |  | i1 | i2 | i3 | i4 |
| TEMPERATURE | t1 | O11 | O12 | O13 | O14 |
|  | t2 | O21 | O22 | O23 | O24 |
|  | t3 | O31 | O32 | O33 | O34 |
|  | t4 | O41 | O42 | O43 | O44 |

FIG. 8

TBL2

|  |  | SENSITIVITY |
|---|---|---|
| TEMPERATURE | t1 | K1 |
|  | t2 | K2 |
|  | t3 | K3 |
|  | t4 | K4 |

FIG. 10

TBL3

| | | CORRECTION SELECTION | |
|---|---|---|---|
| | | LD CONTROL | IMAGE PROCESSING |
| TEMPERATURE | t1 | ○ | — |
| | t2 | ○ | — |
| | t3 | ○ | — |
| | t4 | ○ | — |
| | t5 | — | ○ |

FIG. 13

TBL4

| TEMPERATURE | | PEAK WAVELENGTH |
|---|---|---|
| | t1 | λ1 |
| | t2 | λ2 |
| | t3 | λ3 |
| | t4 | λ4 |

FIG. 14

TBL5

| | | PEAK WAVELENGTH | | | |
|---|---|---|---|---|---|
| | | λ1 | λ2 | λ3 | λ4 |
| TEMPERATURE | t1 | K11 | K12 | K13 | K14 |
| | t2 | K21 | K22 | K23 | K24 |
| | t3 | K31 | K32 | K33 | K34 |
| | t4 | K41 | K42 | K43 | K44 |

FIG. 15

| | | GAIN COEFFICIENT |
|---|---|---|
| WAVELENGTH | λ1 | G1 |
| | λ2 | G2 |
| | λ3 | G3 |
| | λ4 | G4 |

TBL6

FIG. 16

| | | WB COEFFICIENT | |
|---|---|---|---|
| | | B/G | R/G |
| WAVELENGTH | λ1 | B1 | R1 |
| | λ2 | B2 | R2 |
| | λ3 | B3 | R3 |
| | λ4 | B4 | R4 |

TBL7

ENDOSCOPE AND ENDOSCOPE SYSTEM FOR CONTROLLING AMOUNT OF ILLUMINATION LIGHT OF LIGHT SOURCE

CROSS REFERENCE TO RELATED APPLICATION

This application is a continuation application of PCT/JP2018/024337 filed on Jun. 27, 2018, the entire contents of which are incorporated herein by this reference.

BACKGROUND OF THE INVENTION

1. Field of the Invention

The present invention relates to an endoscope system, a light source device for an endoscope, and an endoscope.

2. Description of the Related Art

Endoscopes have been widely used in a medical field and an industrial field. For example, the endoscope has an elongated insertion portion, and radiates illumination light from an illumination window at a distal end portion of the insertion portion, and reflected light of the illumination light from a subject enters an observation window at the distal end portion. An endoscope system has a light source that emits illumination light, and an amount of the illumination light emitted from the light source is controlled so that an endoscope image has a desired brightness.

Generally, an amount of light emitted from the light source is controlled based on an output of a light receiving element that receives a part of the emitted light. For example, Japanese Unexamined Patent Application Publication No. 2012-94891 discloses a technique of providing an optical sensor at a position irradiated with a laser beam, and controlling an optical output of a semiconductor laser chip.

Further, as a temperature of a light source changes, an amount and a wavelength of light emitted from the light source also change. Therefore, for example, Japanese Unexamined Patent Application Publication No. 2017-207412 discloses a technique of including a light sensor that detects the amount of light emitted from the light source and a temperature detection mechanism that detects the temperature of the light source, and keeping luminance and chromaticity of the light source constant even when the temperature of the light source is changed. Therefore, these techniques may be applied to an endoscope system.

SUMMARY OF THE INVENTION

An endoscope system according to an aspect of the present invention includes a light source for an endoscope configured to emit illumination light having a controllable amount of light, an image pickup device configured to output an image pickup signal of an image obtained by receiving reflected light of the illumination light, a light receiving element configured to receive a part of the illumination light of the light source, a first temperature sensor configured to detect a first temperature of the light source, a second temperature sensor configured to detect a second temperature of the light receiving element, a received light amount correction circuit configured to correct an amount of light received by the light receiving element based on the second temperature, and a drive control circuit configured to control driving of the light source so that an amount of the illumination light becomes a set value based on a corrected amount of received light corrected by the received light amount correction circuit and the first temperature.

A light source device for an endoscope according to one aspect of the present invention includes a light source capable of controlling an amount of light, a light receiving element configured to receive a part of illumination light from the light source, a first temperature sensor configured to detect a first temperature of the light source, a second temperature sensor configured to detect a second temperature of the light receiving element, a received light amount correction circuit configured to correct an amount of light received by the light receiving element based on the second temperature, and a drive control circuit configured to control driving of the light source so that an amount of the illumination light becomes a set value based on a corrected amount of received light corrected by the received light amount correction circuit and the first temperature.

An endoscope according to an aspect of the present invention includes the light source device for an endoscope of one aspect of the present invention.

BRIEF DESCRIPTION OF THE DRAWINGS

FIG. 7 is a diagram illustrating an example of a table in which driving conditions of the laser diode are determined according to the first embodiment of the present invention.

FIG. 8 is a diagram illustrating an example of a table in which a sensitivity coefficient of the photodiode is determined according to the first embodiment of the present invention.

FIG. 10 is a diagram illustrating an example of a table according to a modification of the first embodiment of the present invention.

FIG. 13 is a diagram illustrating an example of a table in which a peak wavelength of the laser diode corresponding to a temperature is determined according to the second embodiment of the present invention.

FIG. 14 is a diagram illustrating an example of a table in which a sensitivity coefficient of a photodiode is determined according to the second embodiment of the present invention.

FIG. 15 is a diagram illustrating an example of a table for correcting a difference in amount of light according to a modification of the second embodiment of the present invention.

FIG. 16 is a diagram illustrating an example of a table for correcting a difference in wavelength of illumination light according to the modification of the second embodiment of the present invention.

DETAILED DESCRIPTION OF THE PREFERRED EMBODIMENTS

Hereinafter, embodiments of the present invention will be described.

First Embodiment (Configuration)

Figure 1:
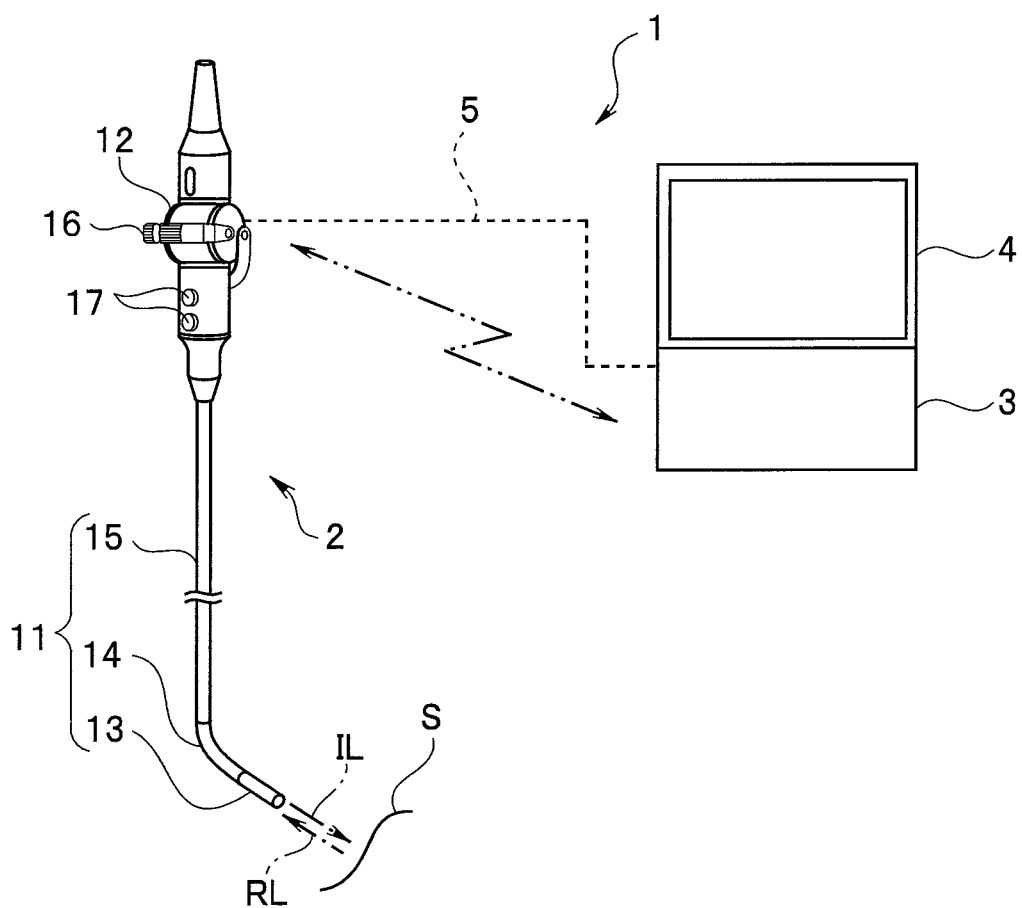
FIG. 1 is a configuration diagram of an endoscope system according to a first embodiment of the present invention.

FIG. 1 is a configuration diagram of an endoscope system according to an embodiment of the present invention.

An endoscope system 1 includes an endoscope 2, a main body portion 3, and a display portion 4. As indicated by a chain double-dashed line, the endoscope 2 and the main body portion 3 are capable of wirelessly communicating with each other. The main body portion 3 and the display portion 4 are connected to each other by a not-illustrated signal cable.

The endoscope 2 includes an elongated insertion portion 11 and an operation portion 12. The insertion portion 11 has, in order, a distal end portion 13, a bending portion 14, and a flexible tube portion 15 from the distal end. A proximal end of the flexible tube portion 15 is connected to the operation portion 12.

The operation portion 12 includes a bending operation lever 16 and various operation buttons 17. A user of the endoscope 2 can bend the bending portion 14 in a desired direction by grasping the operation portion 12 and operating the bending operation lever 16.

Further, the user can freeze an endoscope image or record a frozen still image in a storage device of the main body portion 3 by operating the various operation buttons 17.

An observation window and an illumination window are provided at the distal end portion 13, and an illumination light IL is emitted from the illumination window to a subject S, and a reflected light RL of the illumination light IL from the subject S enters the observation window. The reflected light RL passes through an image pickup optical system, and forms an image on a light receiving surface of an image pickup device 48 (FIG. 2) in the distal end portion 13. An image pickup signal from the image pickup device 48 is transmitted to the main body portion 3 wirelessly. The endoscope image generated based on the image pickup signal from the endoscope 2 is displayed on the display portion 4.

Note that, although the endoscope 2 is configured to be driven by a battery and the endoscope 2 and the main body portion 3 are configured to communicate with each other wirelessly, the endoscope 2 and the main body portion 3 may be connected to each other by a cable 5 as indicated by a dotted line. In that case, power supply to the endoscope 2 is performed via the cable 5, and the communication between the endoscope 2 and the main body portion 3 is also performed via a signal line in the cable 5.

Figure 2:
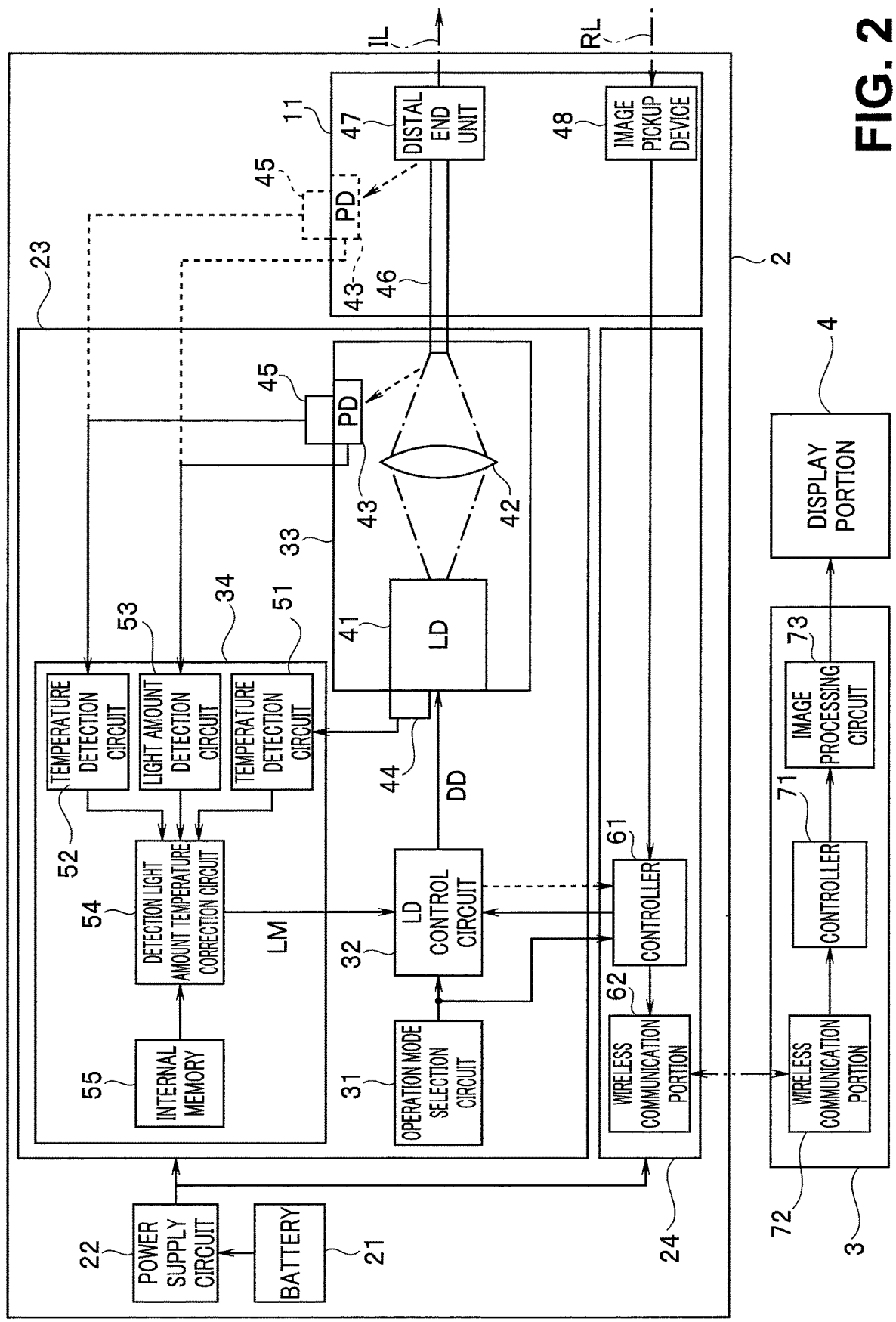
FIG. 2 is a block diagram illustrating a configuration of the endoscope system according to the first embodiment of the present invention.

FIG. 2 is a block diagram illustrating a configuration of the endoscope system 1.

The endoscope 2 includes a battery 21, such as a secondary battery, and a power supply circuit 22. The power supply circuit 22 receives an electric power from the battery 21, generates various voltages required by respective circuits in the endoscope 2, and supplies the generated voltages to the respective circuits.

The endoscope 2 further includes a light source device 23 and an image acquisition device 24.

The battery 21, the power supply circuit 22, the light source device 23, and the image acquisition device 24 are provided in the operation portion 12 of the endoscope 2.

The light source device 23 includes an operation mode selection circuit 31, a laser diode control circuit (hereinafter referred to as an LD control circuit) 32, a light emitting portion 33, and a detection light amount temperature correction portion 34. The light emitting portion 33 includes a light source capable of controlling the amount of light. In other words, the light source device 23 emits illumination light by a light source for an endoscope capable of controlling the amount of light.

The operation mode selection circuit 31 outputs an instruction signal corresponding to an operation of the user to the LD control circuit 32. The user can give various commands to the endoscope 2 by operating the various operation buttons 17. The operation mode selection circuit 31 is a circuit that outputs an instruction signal corresponding to the command signal to the laser diode control circuit 32 and a controller 61, which will be described later. For example, the instruction signal outputted from the operation mode selection circuit 31 includes a selection signal of a normal observation mode by white light.

The LD control circuit 32 includes a processor, and the processor includes a central processing unit (CPU), a ROM, and a RAM. The LD control circuit 32 receives a light amount signal LM indicating an amount of the illumination light from the detection light amount temperature correction portion 34. As will be described later, the LD control circuit 32 configures a driving controller that outputs a drive signal DD for controlling driving of the light source of the light emitting portion 33 so that the amount of the illumination light becomes a set value based on a temperature T1 of a laser diode 41 and the light amount signal LM. In other words, the drive signal DD is determined based on the light amount signal LM from the detection light amount temperature correction portion 34.

As will be described later, a detection light amount temperature correction circuit 54 configures a received light amount correction portion that outputs the light amount signal LM obtained by correcting an amount of light received by a photodiode 43 based on a temperature of the photodiode 43 detected by a thermistor 45.

Further, the LD control circuit 32 operates in response to the instruction signal from the operation mode selection circuit 31 and a control signal from the controller 61. For example, when the operation mode is the normal observation mode, the LD control circuit 32 generates the drive signal DD corresponding to a dimming level from the controller 61.

The light emitting portion 33 incorporates a laser diode (LD) 41 as a semiconductor light-emitting element, a condenser lens 42, and the photodiode (PD) 43 as an optical sensor. The photodiode 43 is provided in the operation portion 12 of the endoscope 2 or in a portion in the vicinity of the operation portion 12.

A thermistor 44 is provided in the laser diode 41 that is a light source. The thermistor 44 is a temperature sensor that detects a temperature of the laser diode 41 that is a light source, and is provided in the vicinity of the laser diode 41 on a substrate on which the laser diode 41 is mounted. In other words, the thermistor 44 is thermally connected to the laser diode 41.

A thermistor 45 is provided in the photodiode 43. The thermistor 45 is a temperature sensor that detects a temperature of the photodiode 43 which is provided in the light emitting portion 33 and which is a light receiving element, and is provided in close contact with or in the vicinity of the photodiode 43. In other words, the thermistor 45 is thermally connected to the photodiode 43. The attachment structure of the thermistor 45 will be described later.

The laser diode 41 emits light in accordance with the drive signal DD that is a drive current from the laser diode control circuit 32.

The condenser lens 42 condenses laser light from the laser diode 41 and condenses the laser light on the end surface of a proximal end portion of an optical fiber 46 connected to the light emitting portion 33. Light entering the end surface of the proximal end portion of the optical fiber 46 passes through an inside of the optical fiber 46 as illumination light and is emitted from an end surface of a distal end portion of the optical fiber 46.

Note that, in general, the optical fiber 46 is divided into two branches in the middle so that the illumination light is emitted from two illumination windows of the distal end portion 13. However, the branching is omitted and not illustrated here.

The light from the condenser lens 42 is condensed on the end surface of the proximal end portion of the optical fiber 46, while the photodiode 43 is disposed at a position where the light reflected by the end surface of the proximal end portion of the optical fiber 46 can be received. In other words, the photodiode 43 is a light receiving element provided in the light emitting portion 33 so as to receive a part of the illumination light of the laser diode 41 that is a light source. An amount of light received by the photodiode 43 is proportional to an amount of laser light emitted from the laser diode 41.

As described above, the endoscope 2 includes the optical fiber 46 for guiding the illumination light, and the photodiode 43 that is the light receiving element is arranged in the vicinity of an incident end of the illumination light of the optical fiber 46.

The light emitting portion 33 and the optical fiber 46 have a pigtail-type structure, and the light emitting portion 33 and the optical fiber 46 are formed integrally with each other. Therefore, the optical fiber 46 extends from the light emitting portion 33.

Figure 3:
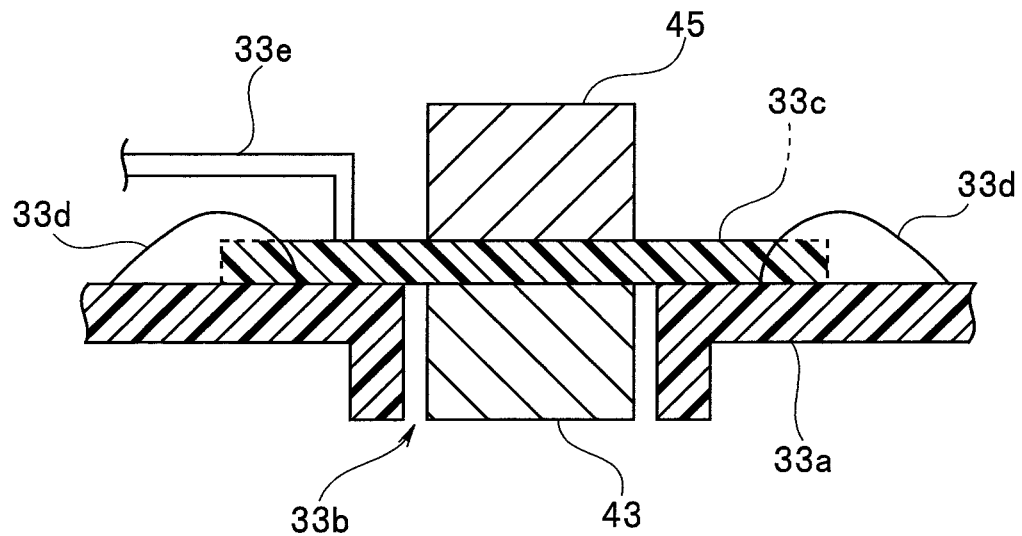
FIG. 3 is a partial cross-sectional view illustrating an attachment structure of a photodiode according to the first embodiment of the present invention.

FIG. 3 is a partial cross-sectional view illustrating an attachment structure of the photodiode 43.

The light emitting portion 33 has a housing 33a for holding the laser diode 41, the lens 42, and the like. An opening 33b is provided in the housing 33a of the light emitting portion 33. A flexible substrate 33c is fixed to the housing 33a by an adhesive 33d so as to cover the opening 33b. The photodiode 43 and the thermistor 45 are mounted on a back surface and a front surface of the flexible substrate 33c, respectively, so as to sandwich the flexible substrate 33c therebetween.

The photodiode 43 is arranged in the housing 33a. In other words, in order to allow the thermistor 45 to accurately detect the temperature of the photodiode 43 through the flexible substrate 33c, the photodiode 43 and the thermistor 45 are mounted on the flexible substrate 33c with the flexible substrate 33c, which is a circuit board, interposed therebetween.

An output signal of the photodiode 43 and an output signal of the thermistor 45 are supplied to a light amount detection circuit 53 and a temperature detection circuit 52 through a plurality of signal lines 33e connected to the flexible substrate 33c, respectively.

Referring back to FIG. 2, the optical fiber 46 is inserted into the insertion portion 11. As described above, the proximal end portion of the optical fiber 46 is connected to the light emitting portion 33, while the distal end portion of the optical fiber 46 is connected to a distal end unit 47 provided in the distal end portion 13. The distal end unit 47 of the endoscope 2 includes a phosphor, and is disposed on a rear side of the illumination window (not illustrated) of the distal end portion 13.

Figure 4:
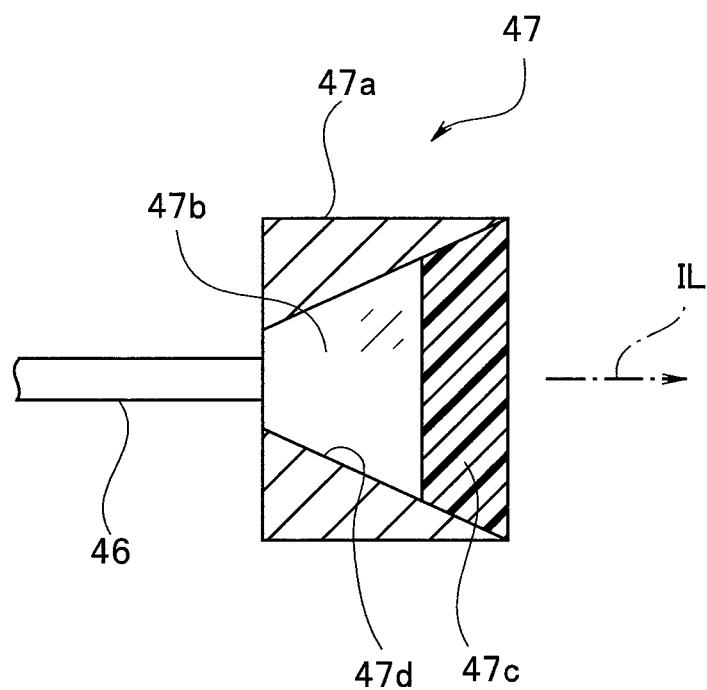
FIG. 4 is a configuration diagram of a distal end unit according to the first embodiment of the present invention.

FIG. 4 is a configuration diagram of the distal end unit 47.

The distal end unit 47 includes a holder 47a, a transparent member 47b, and a phosphor 47c. The phosphor 47c contains diffusion particles (not illustrated).

The holder 47a has an inner peripheral surface 47d having a partial conical shape or a tapered shape, and a reflective film by silver vapor deposition is formed on the inner peripheral surface.

The distal end portion of the optical fiber 46 is connected to the holder 47a so that light from the end surface of the distal end portion of the optical fiber 46 is radiated in the transparent member 47b.

The light entering inside the transparent member 47b from the optical fiber 46 travels straight, and diffused light is reflected by an inner peripheral surface 47d and then enters the phosphor 47c. The phosphor 47c fluoresces in response to the received light, thereby converting a wavelength of the light.

The inner peripheral surface 47d reflects a part of the light emitted from the phosphor 47c, and the light emitted from a distal end surface of the optical fiber 46 and the light emitted from the phosphor 47c mix with each other and are emitted from a distal end portion of the distal end unit 47.

Here, the subject is irradiated with white light for normal observation as the illumination light. For this reason, the laser diode 41 emits blue laser light. The phosphor 47c is a yellow phosphor, and is excited by receiving the blue laser light to emit yellow fluorescence. As a result, mixed light of the blue diffused light and the yellow fluorescence becomes white light, and is emitted from the illumination window.

In other words, the endoscope 2 includes the phosphor 47c that converts a wavelength of a part of light emitted from the light source, and the illumination light is mixed light of the light emitted from the light source and the wavelength-converted light.

Note that, in FIG. 2, as indicated by a dotted line, the photodiode 43 and the thermistor 45 may be arranged in the vicinity of the distal end unit 47. In other words, the photodiode 43 may be disposed at the distal end portion 13 so as to receive a part of the light emitted from the end surface of the distal end portion of the optical fiber 46.

Referring back to FIG. 2, the image pickup device 48 is arranged in the distal end portion 13 of the insertion portion 11. An image pickup optical system (not illustrated) is disposed on the rear side of the observation window of the distal end portion 13, and the image pickup device 48 is disposed at a position in which light that has passed through the image pickup optical system is received. The image pickup device 48 is, for example, a CMOS image sensor.

The detection light amount temperature correction portion 34 includes a temperature detection circuit 51 and the temperature detection circuit 52, the light amount detection circuit 53, the detection light amount temperature correction circuit 54, and an internal memory 55.

The temperature detection circuit 51 is connected to the thermistor 44, detects the temperature of the laser diode 41, and outputs a signal of the detected temperature.

The temperature detection circuit 52 is connected to the thermistor 45, detects the temperature of the photodiode 43, and outputs a signal of the detected temperature.

The light amount detection circuit 53 is connected to the photodiode 43, detects an amount of light received by the photodiode 43, and outputs a signal of the detected light amount.

The detection light amount temperature correction circuit 54 includes a processor, and the processor includes a central processing unit (CPU), a ROM, and a RAM. The detection light amount temperature correction circuit 54 outputs the light amount signal LM obtained by performing temperature correction on the light amount signal from the light amount detection circuit 53 by using various types of table data stored in the internal memory 55 based on the temperature signal from the temperature detection circuit 52.

Generation processing of the light amount signal LM in the detection light amount temperature correction circuit 54 will be described later.

The internal memory 55 stores a table for storing various types of data to be described later.

The image acquisition device 24 includes the controller 61 that receives an image pickup signal from the image pickup device 48, and a wireless communication portion 62. The image acquisition device 24 acquires an image by receiving the image pickup signal obtained by receiving reflected light of the illumination light.

More specifically, the controller 61 is a circuit that receives the image pickup signal from the image pickup device 48 and compresses the image pickup signal. The controller 61 outputs the compressed image pickup signal to the wireless communication portion 62.

The controller 61 also performs light control processing and the like based on the received image pickup signal.

The wireless communication portion 62 is a circuit for performing wireless communication using a predetermined frequency band. The wireless communication portion 62 transmits the compressed image pickup signal to the main body portion 3.

The main body portion 3 includes a controller 71, a wireless communication portion 72, and an image processing circuit 73.

The controller 71 includes a processor, and the processor includes a central processing unit (CPU), a ROM, and a RAM.

The wireless communication portion 72 is a circuit that communicates with the wireless communication portion 62 of the endoscope 2. The wireless communication portion 72 receives a wireless signal of an image pickup signal from the wireless communication portion 62, and outputs the wireless signal to the controller 71. Since the received image pickup signal is compressed, the controller 71 decompresses the received image pickup signal, and outputs the decompressed image pickup signal to the image processing circuit 73.

The image processing circuit 73 performs various kinds of image processing such as gamma correction, and generates a display signal. The display signal is output to the display portion 4.

When the user selects the normal observation mode, the white illumination light IL is radiated to the subject from the distal end portion 13 of the insertion portion 11, and a subject image caused by the reflected light RL from the subject is imaged on an image pickup surface of the image pickup device 48. The image pickup signal obtained by the image pickup device 48 is compressed, and the compressed image pickup signal is transmitted from the endoscope 2 to the main body portion 3 wirelessly.

The main body portion 3 decompresses the image pickup signal received wirelessly, performs image processing on the decompressed image pickup signal, and outputs to the display portion 4 an image signal of the endoscope image subjected to the image processing. Therefore, the user can perform endoscopy and the like by viewing the endoscope image displayed on the display portion 4.

Figure 5:
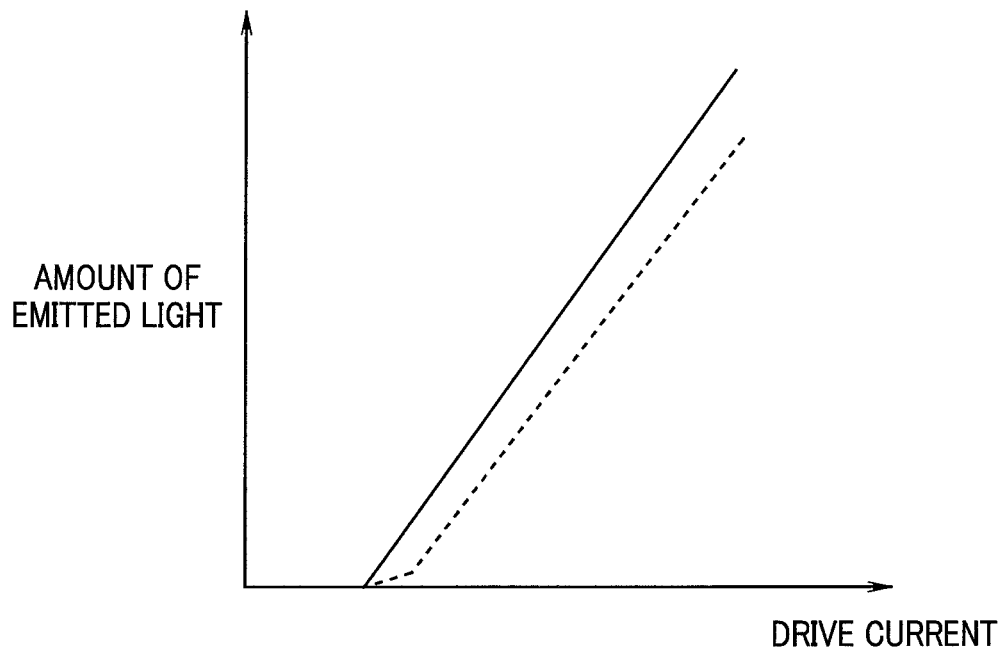
FIG. 5 is a diagram illustrating temperature characteristics of a laser diode according to the first embodiment of the present invention.

Here, temperature characteristics of the laser diode 41 will be described. FIG. 5 is a diagram illustrating the temperature characteristics of the laser diode 41.

As illustrated in FIG. 5, an amount of light emitted from the laser diode 41 increases in proportion to the drive current of the laser diode 41. A solid line indicates a relationship between the drive current and the amount of emitted light when the temperature of the laser diode 41 is Ta, and a dotted line indicates a relationship between the drive current and the amount of emitted light when the temperature of the laser diode 41 is Tb higher than Ta. Here, it has been shown that when the temperature of the laser diode 41 increases, the amount of emitted light decreases. Therefore, the amount of light emitted from the laser diode 41 has the temperature characteristics.

Figure 6:
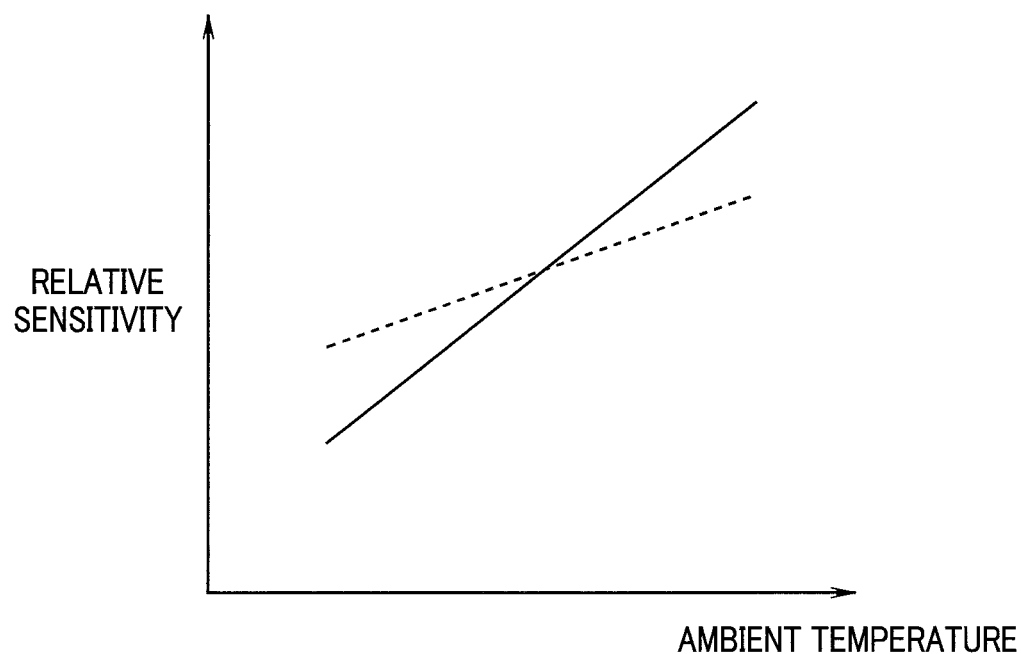
FIG. 6 is a diagram illustrating temperature characteristics of a relative sensitivity of the photodiode according to the first embodiment of the present invention.

FIG. 6 illustrates temperature characteristics of the photodiode 43. FIG. 6 is a diagram illustrating the temperature characteristics of a relative sensitivity of the photodiode 43.

As illustrated in FIG. 6, the relative sensitivity of the photodiode 43 increases in proportion to an ambient temperature of the photodiode 43. In other words, the relative sensitivity of the photodiode 43 increases in proportion to an increase in the ambient temperature of the photodiode 43. The relative sensitivity also varies depending on the wavelength of the received light. A solid line and a dotted line in FIG. 6 indicate changes in the relative sensitivity with respect to the changes in the ambient temperature for light beams having different wavelengths. Therefore, the relative sensitivity of the photodiode 43 has the temperature characteristics.

When the laser diode 41 and the photodiode 43 are arranged so as to be spaced apart from each other, the temperature change of the laser diode 41 and the temperature change of the photodiode 43 do not coincide with each other.

(Operation)

In the endoscope system 1, the driving of the light source is controlled so that the amount of the illumination light becomes a set value. The amount of the illumination light is detected by the photodiode 43, but a detection light amount of the photodiode 43 has the temperature characteristics, and thus the temperature correction on the detection light amount of the illumination light is performed.

The temperature correction of the detection light amount of the illumination light by the photodiode 43 will be described.

First, table data used for the temperature correction of the detection light amount will be described.

Tables TBL1 and TBL2 are stored in the internal memory 55.

FIG. 7 is a diagram illustrating an example of the table TBL1 that defines driving conditions of the laser diode 41.

The table TBL1 stores an output value of the laser diode 41 (hereinafter referred to as an LD output value) corresponding to the temperature T1 of the laser diode 41 and the driving conditions of the laser diode 41, i. e., an emitted light amount value. The driving condition of the laser diode 41 is, for example, a drive current value.

As illustrated in FIG. 5, the amount of light emitted from the laser diode 41 is changed depending on the temperature T1 of the laser diode 41, that is, the amount of emitted light has a temperature characteristic.

Respective temperatures t1, t2, t3, and t4 of the table TBL1 illustrated in FIG. 7 define the range of the temperature T1 of the laser diode 41. Similarly, i1, i2, i3, and i4 as each driving condition of the table TBL1 define the range of the driving condition, in this case, the range of the drive current of the laser diode 41.

For example, in FIG. 7, the LD output value O23 is an amount of emitted light when the temperature T1 of the laser diode 41 is in the range of the temperature t2 and the driving condition is in the range of i3. In other words, FIG. 7 shows that, when the temperature T1 of the laser diode 41 is the temperature t2, it is necessary to supply the drive current i3 to the laser diode 41 in order to obtain the amount of emitted light of O23.

Therefore, the table TBL1 is a table in which the LD output value (i. e., the emitted light amount value) corresponding to the temperature T1 of the laser diode 41 and the driving condition of the laser diode 41 is set. In other words, the table TBL1 indicates the relationship between the temperature T1 and the drive current for obtaining the desired amount of emitted light.

FIG. 8 is a diagram illustrating an example of the table TBL2 that defines a sensitivity coefficient of the photodiode 43.

The table TBL2 stores a sensitivity coefficient K corresponding to a temperature T2 of the photodiode 43. In FIG. 8, the respective temperatures t1, t2, t3, and t4 in the table TBL2 define the temperature range, as in FIG. 7.

In the photodiode 43, the sensitivity coefficient K varies depending on the temperature T2 of the photodiode 43. As illustrated in FIG. 6, the sensitivity coefficients K of the photodiode 43 also differ depending on the wavelength of the received light.

The sensitivity coefficient is sensitivity data indicating a change amount or a change rate of the sensitivity of the photodiode 43 depending on the temperature. Therefore, the table TBL2 stores the sensitivity data of the photodiode 43 corresponding to the temperature T2 of the photodiode 43.

Accordingly, the table TBL2 is a table in which the sensitivity coefficient K corresponding to the temperature of the photodiode 43 is set.

Next, the temperature correction of the amount of emitted light in a drive control of the laser diode 41 will be described.

Figure 9:
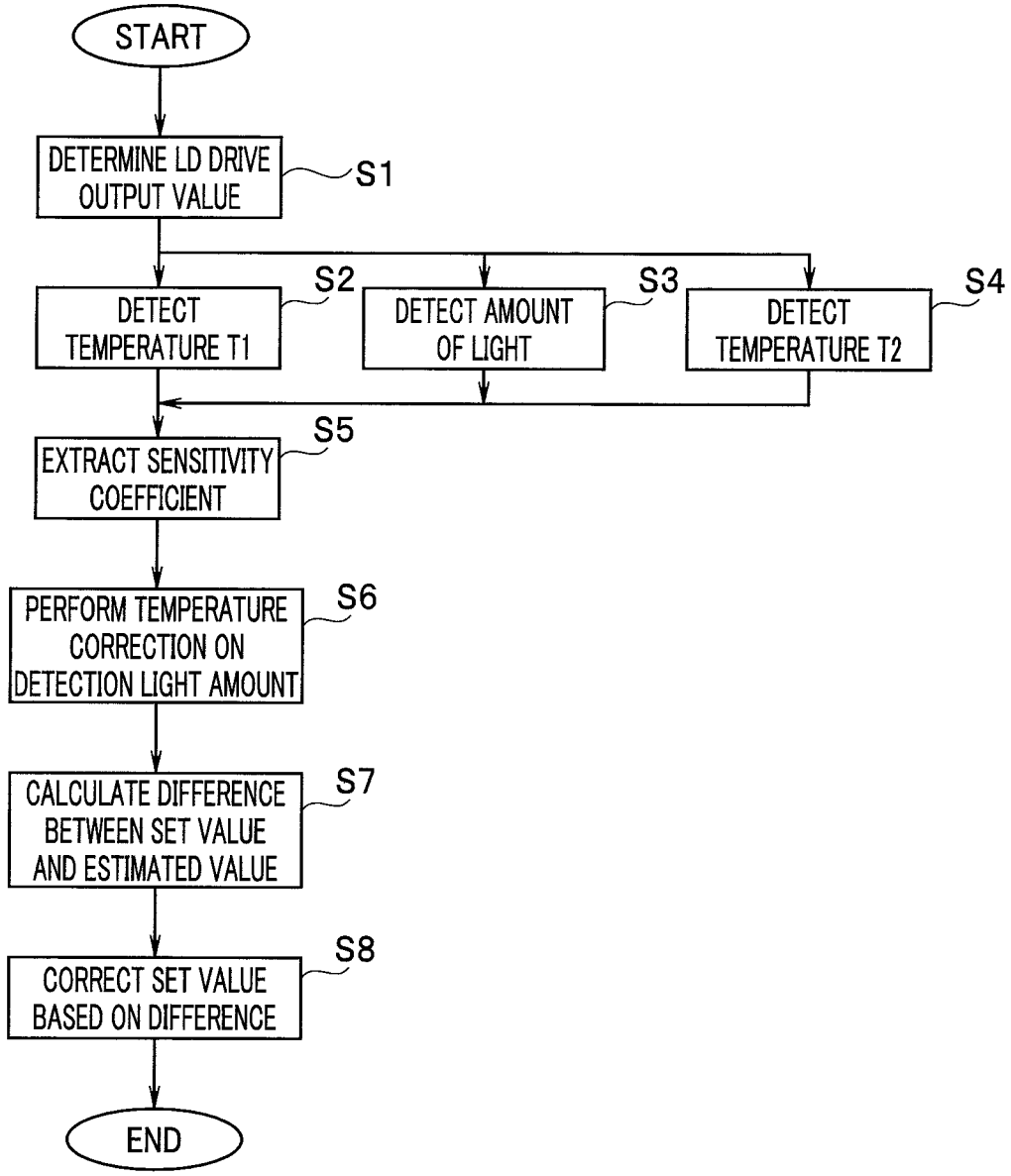
FIG. 9 is a flowchart illustrating an example of a flow of processing of a temperature correction of an amount of light emitted from a light emitting portion and a drive control of a light source according to the first embodiment of the present invention.

FIG. 9 is a flowchart illustrating an example of a flow of processing of the temperature correction of the amount of light emitted from the light emitting portion 33 and the drive control of the light source.

The processing in FIG. 9 is performed in the detection light amount temperature correction circuit 54 and the LD control circuit 32. Here, the CPUs of the detection light amount temperature correction circuit 54 and the LD control circuit 32 read out the program of the ROM and execute the program, whereby the processing of FIG. 9 is performed.

The LD control circuit 32 determines the driving condition (i. e., the drive current value) so that the LD output value (i. e., the emitted light amount value) of the laser diode 41 becomes a LD output set value SSO (step (hereinafter shortly referred to as S) 1). The LD control circuit 32 determines the drive current value based on the temperature T1 of the laser diode 41 with reference to the table TBL1.

For example, assuming that when the temperature T1 of the laser diode 41 is the temperature t1, and the LD output set value SSO of the amount of emitted light is O12, i2 is selected as the drive current value that is the driving condition of the laser diode 41.

As a result, the laser diode 41 is driven according to the driving conditions determined in S1.

The detection light amount temperature correction circuit 54 detects the temperature T1 of the laser diode 41 by the thermistor 44 (S2).

At the same time, the detection light amount temperature correction circuit 54 detects the amount of light emitted from the laser diode 41 by the photodiode 43 (S3).

At the same time, the detection light amount temperature correction circuit 54 detects the temperature T2 of the photodiode 43 by the thermistor 45 (S4).

The detection light amount temperature correction circuit 54 extracts the sensitivity coefficient K from the table TBL2 based on the temperature T2 of the photodiode 43 (S5). For example, when the temperature T2 of the photodiode 43 is the temperature t3, K3 is extracted as the sensitivity coefficient K.

The detection light amount temperature correction circuit 54 corrects the temperature of the detection light amount detected by the photodiode 43 by using the extracted sensitivity coefficient K (S6). In other words, the detection light amount temperature correction circuit 54 corrects the amount of light received by the photodiode 43 by using the table TBL2 for storing the sensitivity data of the photodiode 43 corresponding to the temperature T2 of the photodiode 43.

The LD control circuit 32 calculates an LD output estimated value ESO of the amount of emitted light from the corrected light amount signal LM after the temperature correction, and calculates a difference between the calculated LD output estimated value ESO and the LD output set value SSO (S7).

The LD control circuit 32 corrects the drive signal DD of the amount of light based on the difference calculated in S7 (S8).

More specifically, referring to the table TBL1, the LD control circuit 32 corrects the drive signal DD so that the difference becomes 0 in accordance with the calculated difference and the temperature T1 in the driving conditions in the table TBL1.

In other words, the LD control circuit 32 corrects the drive signal DD for driving the laser diode 41 so that the calculated difference decreases based on a difference between an amount of received light after the correction and the set value and the temperature T1 of the laser diode 41.

As a result, since the LD control circuit 32 outputs the drive signal DD based on the corrected light amount signal LM, the illumination light having an appropriate amount of illumination light is emitted in accordance with the temperature characteristics of the laser diode 41 and the temperature characteristics of the photodiode 43.

As described above, according to the above-described embodiment, it is possible to provide an endoscope system capable of appropriately controlling the amount of the light emitted from the light source even when the temperature of the light source and the temperature of the light sensor are changed.

Next, a modification of the present embodiment will be described.

In the above-described embodiment, brightness of the endoscope image is appropriately controlled by the amount of emitted light of the illumination light. However, the brightness of the endoscope image may be appropriately controlled by also using the image processing based on a temperature of at least one of the laser diode 41 or the photodiode 43.

FIG. 10 is a diagram illustrating an example of a table TBL3 according to the present modification. The table TBL3 is also stored in the internal memory 55 as is the case with TBL1 and TBL2.

FIG. 10 is a diagram illustrating an example of the table TBL3 for determining whether a brightness correction of the endoscope image is performed by the control of the laser diode 41 or by the image processing.

In the table TBL3, it is defined that the brightness correction of the endoscope image is performed by using which one of the control of the laser diode 41 (hereinafter also referred to as LD control) and the image processing, in accordance with a higher temperature of the temperature T1 of the laser diode 41 and the temperature T2 of the photodiode 43.

Note that, although the higher temperature of the temperature T1 of the laser diode 41 and the temperature T2 of the photodiode 43 is used as a reference here, an average value of the temperature T1 of the laser diode 41 and the temperature T2 of the photodiode 43 may be used as a reference, or a predetermined temperature of either one of the temperature T1 of the laser diode 41 and the temperature T2 of the photodiode 43 may be used as the reference.

The respective temperatures t1, t2, t3, t4, and a temperature t5 in the table TBL3 shown in FIG. 10 define the temperature range, as in FIG. 7. In the table TBL3, it is set that when the higher temperature of the temperature T1 of the laser diode 41 and the temperature T2 of the photodiode 43 is within the range from t1 to t4, the brightness correction of the endoscope image is performed by the control of the laser diode 41 (LD control), and when the temperature is t5, the brightness correction of the endoscope image is performed by the image processing.

Figure 11:
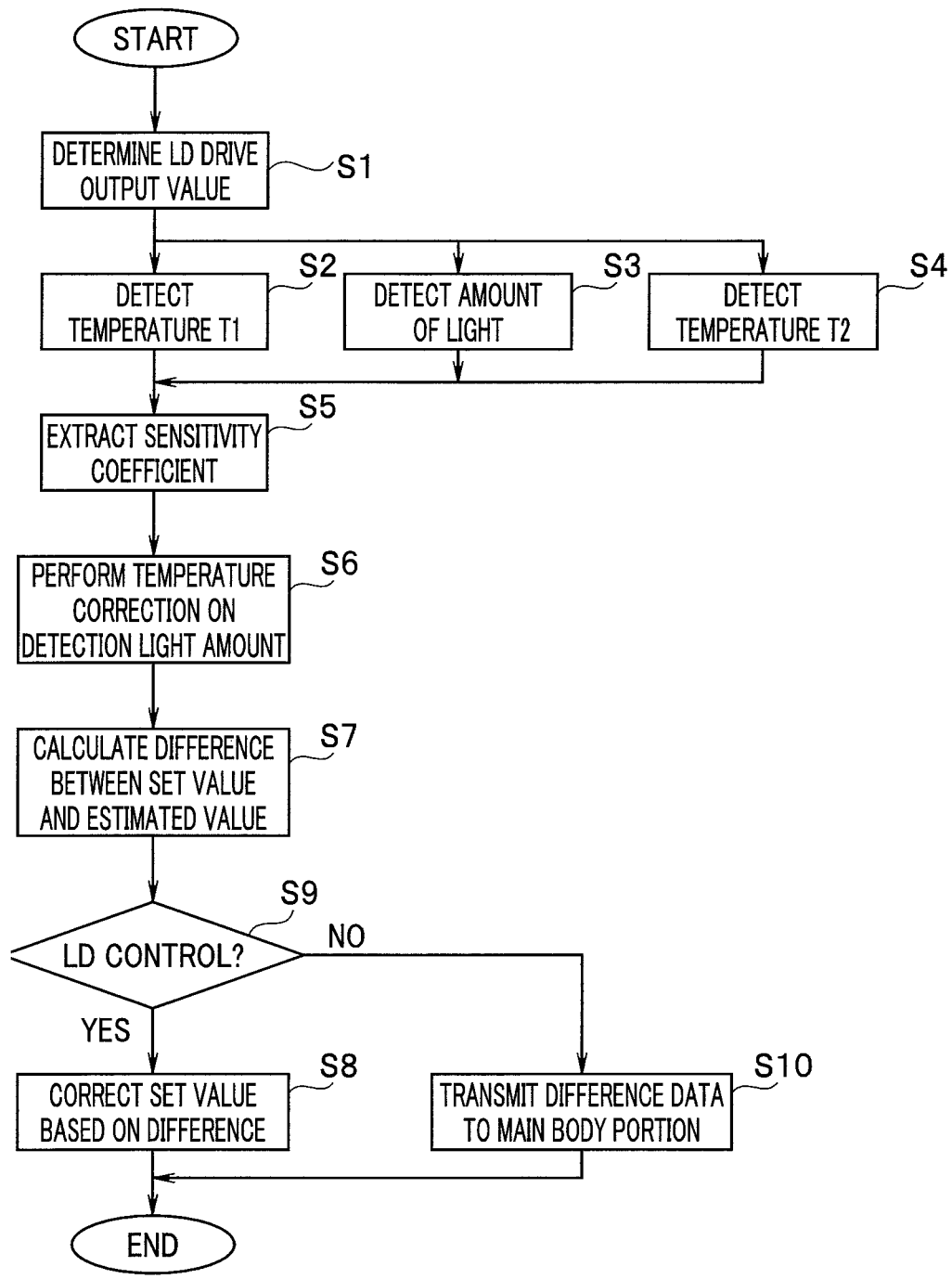
FIG. 11 is a flowchart illustrating an example of a flow of a temperature correction processing of an amount of light emitted from a light emitting portion 33 according to the modification of the first embodiment of the present invention.

FIG. 11 is a flowchart illustrating an example of a flow of temperature correction processing of the amount of light emitted from the light emitting portion 33 according to the present modification.

Note that the same processing as the processing steps in FIG. 9 will be denoted by the same step numbers and description thereof will be omitted, and only different processing will be described.

After the processing from S1 to S8 is performed, the detection light amount temperature correction circuit 54 determines whether the brightness correction of the endoscope image is performed by the LD control based on the table TBL3 (S9). More specifically, referring to the table TBL3, it is determined whether the brightness correction of the endoscope image is performed by the LD control based on the higher temperature of the temperature T1 of the laser diode 41 and the temperature T2 of the photodiode 43.

When the higher temperature of the temperature T1 of the laser diode 41 and the temperature T2 of the photodiode 43 is within the range from t1 to t4, the LD control is selected, and when the temperature is in t5, the image processing is selected.

When it is determined to use the LD control (S9: YES), the detection light amount temperature correction circuit 54 performs the processing of S8.

When it is determined to use the image processing (S9: NO), the detection light amount temperature correction circuit 54 outputs difference data calculated in step S7 to the controller 61, as indicated by a dotted line in FIG. 2, and transmits the difference data to the main body portion 3 from the wireless communication portion 62 (S10).

In the main body portion 3, the wireless communication portion 72 transmits the difference data to the image processing circuit 73 via the controller 71.

The image processing circuit 73 determines a gain corresponding to the received difference data, and corrects the brightness of the endoscope image by multiplying each pixel value of the endoscope image by the gain (S8).

When a heat source, such as the laser diode 41, is arranged in the operation portion 12, a temperature of the operation portion 12 grasped by the user is increased. As such, when the higher temperature of the temperature T1 of the laser diode 41 and the temperature T2 of the photodiode 43 becomes equal to or higher than t5 so that the temperature of the operation portion 12 does not reach the predetermined temperature or higher, the brightness of the image is adjusted by the image processing, and thus it is possible to prevent the operation portion 12 that is grasped by the user from heating.

As described above, when a temperature of at least one of the temperature T1 or the temperature T2 becomes equal to or higher than the predetermined temperature t5, the LD control circuit 32 controls the driving of the light source so that the temperature of the at least one of the temperature T1 or the temperature T2 does not exceed the predetermined temperature t5. Then, when the temperature of at least one of the temperature T1 or the temperature T2 becomes equal to or higher than the predetermined temperature t5, the image processing circuit 73 increases luminance of the image.

As described above, brightness of the endoscope image may be appropriately controlled by using the image processing as well.

Second Embodiment

In the first embodiment, the brightness of the endoscope image is corrected by adjusting the amount of emitted light of the illumination light in consideration of the temperature characteristics of the optical sensor that detects the amount of the illumination light. In a second embodiment, however, the amount of emitted light of the illumination light is also adjusted in consideration of the temperature characteristics of the wavelength of the illumination light.

Since the configuration of the endoscope system of the second embodiment is substantially the same as the configuration of the endoscope system 1 of the first embodiment illustrated in FIG. 1 to FIG. 4, the same constituent elements are denoted by the same reference numerals, and description thereof will be omitted, and only different constituent elements will be described.

As illustrated in FIG. 2, in the endoscope system 1, the distal end unit 47 is provided in the distal end portion 13 of the insertion portion 11. The phosphor 47c that fluoresces when receiving laser light is arranged in the distal end unit 47.

The phosphor 47c has a characteristic in which a fluorescence intensity changes depending on a wavelength band of the laser light that is an excitation light.

Since the illumination light emitted from the illumination window of the distal end portion 13 has a mixed color of blue laser light and yellow fluorescence, the temperature T1 of the laser diode 41 changes and the wavelength of the laser light shifts, so that the intensity of the fluorescence also changes, and a spectral shape of the illumination light also changes.

Figure 12:
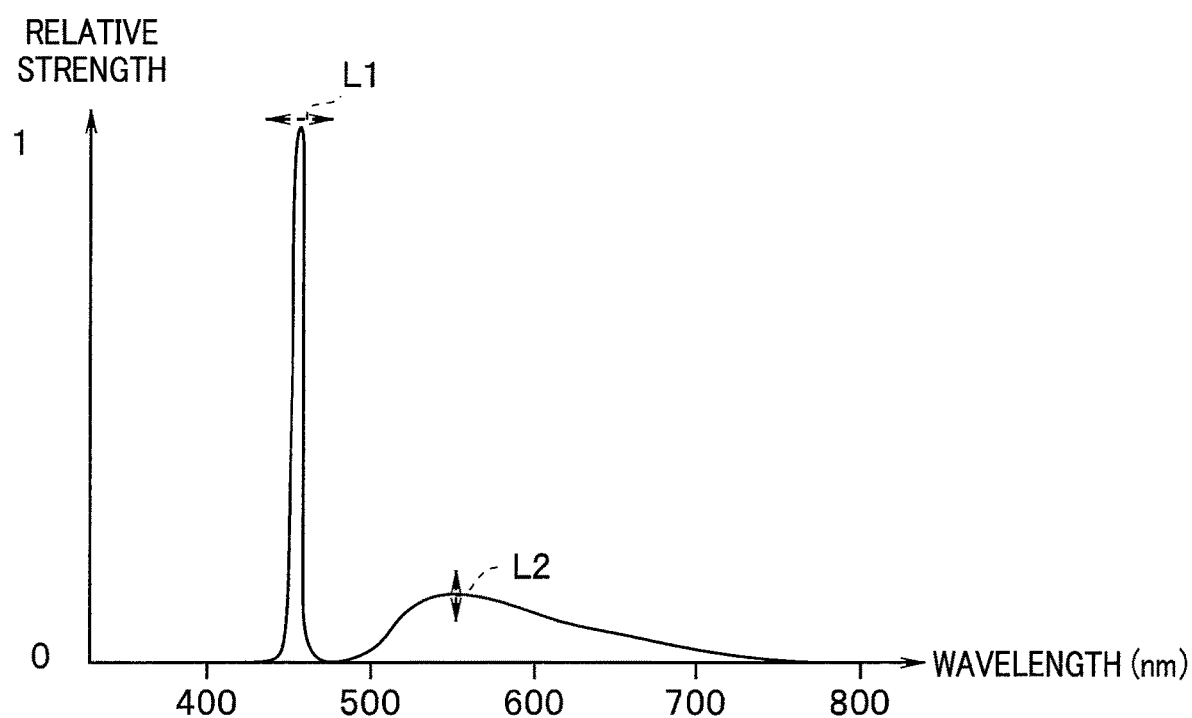
FIG. 12 is a graph illustrating an example of a spectrum of illumination light according to a second embodiment of the present invention.

FIG. 12 is a graph illustrating an example of a spectrum of illumination light.

The illumination light includes the blue laser light of the laser diode 41 and the yellow fluorescence of the phosphor 47c, but a peak wavelength of the laser light of the laser diode 41 varies depending on the temperature, as indicated by a dotted line L1. As indicated by a dotted line L2, fluorescent components in the illumination light also vary in accordance with the fluctuation in the wavelength of the laser light. As a result, hue of the endoscope image also changes.

Therefore, in the present embodiment, the table TBL1 and tables TBL4 and TBL5 are stored in the internal memory 55. The table TBL1 is the table shown in FIG. 7.

FIG. 13 is a diagram illustrating an example of the table TBL4 in which the peak wavelength of the laser diode 41 is determined, the peak wavelength corresponding to the temperature. The table TBL4 is also stored in the internal memory 55.

The table TBL4 stores a peak wavelength $\lambda$ of the laser diode 41 corresponding to the temperature T1. The respective temperatures t1, t2, t3, and t4 in the table TBL4 shown in FIG. 13 define the temperature range, as in FIG. 7.

In the laser diode 41, the peak wavelength $\lambda$ varies depending on the temperature T1 of the laser diode 41.

Therefore, the table TBL4 is a table in which the peak wavelength $\lambda$ corresponding to the temperature of the laser diode 41 is set.

FIG. 14 is a diagram illustrating an example of the table TBL5 that defines a sensitivity coefficient of the photodiode 43.

The table TBL5 stores the sensitivity coefficient K of the photodiode 43 corresponding to the temperature T2 and the peak wavelength $\lambda$ of the photodiode 43. The sensitivity coefficient K of the photodiode 43 differs depending on the temperature T2 of the photodiode 43, and also varies depending on the peak wavelength.

The respective temperatures t1, t2, t3, and t4 of the table TBL5 shown in FIG. 14 define the range of the temperature T2 of the photodiode 43. Similarly, respective peak wavelengths $\lambda 1$, $\lambda 2$, $\lambda 3$, and $\lambda 4$ of the table TBL5 define the range of the peak wavelength of the illumination light. For example, in FIG. 14, a light receiving coefficient K23 is a light receiving coefficient when the temperature T2 of the photodiode 43 is within the range of the temperature t2 and the peak wavelength is within the range of $\lambda 3$.

Therefore, the table TBL5 is a table in which a light receiving coefficient corresponding to the temperature T2 of the photodiode 43 and the peak wavelength $\lambda$ of the illumination light are set.

Next, the temperature correction of the amount of emitted light in the drive control of the laser diode 41 will be described. The temperature correction processing of the amount of light emitted from the light emitting portion 33 in the present embodiment is the same in flow as the processing of FIG. 9 described above, and therefore, the processing of the detection light amount temperature correction circuit 54 will be described with reference to FIG. 9.

The same processing as that in the first embodiment will be briefly described, and only different processing will be described.

In the detection light amount temperature correction circuit 54, for example, assuming that when the temperature T1 of the laser diode 41 is the temperature t1 and the LD output set value SSO of the amount of emitted light is O12, i2 is selected as the drive current value that is the driving condition of the laser diode 41 (S1). At this time, since the temperature T1 of the laser diode 41 is the temperature t1, the peak wavelength of the laser light is $\lambda 1$. The laser diode 41 is driven by the drive current i2.

The detection light amount temperature correction circuit 54 detects the temperature T1 (S2) of the laser diode 41 by the thermistor 44, the amount of light (S3) emitted from the laser diode 41 by the photodiode 43, and the temperature T2 of the photodiode 43 by the thermistor 45 (S4).

The detection light amount temperature correction circuit 54 extracts the sensitivity coefficient K from the tables TBL4 and TBL5 based on the temperature T1 of the laser diode 41 and the temperature T2 of the photodiode 43 (S5). For example, when the temperature T1 of the laser diode 41 is t2, $\lambda 2$ is extracted as the peak wavelength from the table TBL4. When the temperature T2 of the photodiode 43 is the temperature t3, the sensitivity coefficient K32 is extracted from the table TBL5 based on the extracted $\lambda 2$ and the temperature t3.

The detection light amount temperature correction circuit 54 corrects the temperature of the detection light amount detected by the photodiode 43 by using the extracted sensitivity coefficient K (S6).

In other words, the detection light amount temperature correction circuit 54 corrects the amount of light received by the photodiode 43 in consideration of the wavelength of the illumination light corresponding to the temperature T1 of the laser diode 41. Specifically, the detection light amount temperature correction circuit 54 corrects the amount of light received by the photodiode 43 by using the table TBL4 for storing the peak wavelength data of the illumination light corresponding to the temperature T1 of the laser diode 41 and the table TBL5 for storing the sensitivity data corresponding to the temperature T2 and the peak wavelength $\lambda$ of the photodiode 43.

The LD control circuit 32 calculates the LD output estimated value ESO of the amount of emitted light from the corrected light amount signal LM after the temperature correction, and calculates the difference between the calculated LD output estimated value ESO and the LD output set value SSO (S7).

The LD control circuit 32 corrects the drive signal DD of the amount of light based on the difference calculated in S7 (S8).

More specifically, referring to the table TBL1, the LD control circuit 32 corrects the drive signal DD so that the difference becomes 0 in accordance with the calculated difference and the temperature T1 in the driving conditions in the table TBL1.

As a result, since the LD control circuit 32 outputs the drive signal DD based on the corrected light amount signal LM, the illumination light having an appropriate amount of illumination light is emitted in accordance with the temperature characteristics of the laser diode 41 and the temperature characteristics of the photodiode 43.

Further, even when the wavelength of the laser light of the laser diode 41 is shifted due to the temperature, the amount of emitted light of the illumination light is adjusted in consideration of the temperature characteristic of the wavelength.

As described above, according to the above-described embodiment, it is possible to provide an endoscope system capable of appropriately controlling the amount of light emitted from the light source even when the temperature of the light source and the temperature of the light sensor are changed.

Further, since the amount of light of the light source is also adjusted in consideration of the wavelength shift of the laser diode 41 due to the temperature, the brightness of the obtained endoscope image also becomes appropriate.

Next, a modification of the present embodiment will be described.

In the above-described embodiment, the brightness of the endoscope image is appropriately controlled by the amount of emitted light of the illumination light. However, the brightness and color of the endoscope image may be controlled by using the image processing based on a temperature of at least one of the laser diode 41 or the photodiode 43.

In a memory (not illustrated) of the main body portion 3, tables TBL6 and TBL7 are stored.

FIG. 15 is a diagram illustrating an example of the table TBL6 for correcting a difference in the amount of light according to the modification of the second embodiment.

The table TBL6 is a table in which a gain coefficient corresponding to the peak wavelength of the illumination light is set.

The respective wavelengths λ1, λ2, λ3, and λ4 in the table TBL6 illustrated in FIG. 15 define the range of the peak wavelength. Here, gain coefficients G1, G2, G3, and G4 are stored in the table TBL6 corresponding to the four wavelengths λ1, λ2, λ3, and λ4, respectively.

FIG. 16 is a diagram illustrating an example of the table TBL7 for correcting a difference in wavelength of the illumination light according to the modification of the second embodiment.

Table TBL7 is a table in which a white balance coefficient corresponding to the peak wavelength of the illumination light is set.

The respective wavelengths λ1, λ2, λ3, and λ4 in the table TBL6 shown in FIG. 16 define the range of the peak wavelength as in FIG. 15. Here, corresponding to four wavelengths λ1, λ2, λ3, and λ4, B1, B2, B3, and B4 and R1, R2, R3, and R4 are stored in the table TBL7 as B/G (blue/green) and as R/G (red/green), respectively.

Since the temperature correction processing of the amount of light emitted from the light emitting portion 33 in the present modification is the same in flow as the processing in FIG. 11 described above, the processing of the detection light amount temperature correction circuit 54 will be described with reference to FIG. 11.

The same processing as that in the first and second embodiments will be briefly described, and only different processing will be described.

Note that the same processing as the processing steps in FIG. 11 will be denoted by the same step numbers and description thereof will be omitted, and only different processing will be described.

After performing the processing from S1 to S6, the detection light amount temperature correction circuit 54 calculates a difference s1 between the LD output estimated value ESO calculated in S6 and the LD output set value SSO, and also calculates a difference s2 between the set value and the estimated value of the peak wavelength (S7).

The detection light amount temperature correction circuit 54 determines whether the brightness correction of the endoscope image is performed by the LD control based on the table TBL3 (S9).

When the higher temperature of the temperature T1 of the laser diode 41 and the temperature T2 of the photodiode 43 is within the range from t1 to t4, the LD control is selected. When the temperature is in t5, the image processing is selected.

When it is determined to use the LD control, the detection light amount temperature correction circuit 54 performs the processing of S8.

When it is determined to use the image processing, the detection light amount temperature correction circuit 54 outputs the calculated difference data s1 and s2 to the controller 61, as indicated by the dotted line in FIG. 2. The difference data s1 and s2 are transmitted from the image acquisition device 24 to the main body portion 3 (S10).

The difference data is transmitted from the wireless communication portion 72 of the main body portion 3 to the image processing circuit 73 via the controller 71.

The image processing circuit 73 calculates a gain adjustment amount so that the received difference s1 becomes 0 from the difference in gain coefficient between the wavelengths in the table TBL6 in FIG. 15, and adds the gain adjustment amount to each pixel value in the endoscope image, thereby correcting the brightness of the endoscope image.

The image processing circuit 73 further calculates a white balance adjustment amount so that the received difference s2 becomes 0 from the difference in white balance coefficient between the wavelengths in the table TBL7 in FIG. 16, and adds the white balance adjustment amount to each pixel value in the endoscope image, thereby correcting the color of the endoscope image.

As described above, when the temperature of at least one of the temperature T1 or the temperature T2 becomes equal to or higher than the predetermined temperature t5, the LD control circuit 32 controls the driving of the light source so that the temperature of the at least one of the temperature T1 or the temperature T2 does not exceed the predetermined temperature t5. Then, when the temperature of at least one of the temperature T1 or the temperature T2 becomes equal to or higher than the predetermined temperature t5, the image processing circuit 73 increases the luminance of the image and also adjusts the color of the image.

As described above, the brightness and the color of the endoscope image may be appropriately adjusted by using the image processing as well.

As described above, according to each of the embodiments and each of the modifications described above, it is possible to provide an endoscope system, a light source device for an endoscope, and an endoscope that are capable of appropriately controlling the amount of the light emitted from the light source, even when the temperature of the light source and the temperature of the light sensor are changed.

The present invention is not limited to the embodiments described above, and various changes and modifications can be made without departing from the spirit and scope of the present invention.

What is claimed is:

1. An endoscope comprising:
  a light source for an endoscope configured to emit illumination light having a controllable amount of light;
  an image sensor configured to output an image pickup signal of an image obtained by receiving reflected light of the illumination light;

an optical sensor configured to receive a part of the illumination light of the light source;

a first temperature sensor configured to detect a first temperature of the light source;

a second temperature sensor configured to detect a second temperature of the optical sensor: and a controller comprising hardware, the controller being configured to:

correct an amount of light received by the optical sensor based on the second temperature;

control driving of the light source so that an amount of the illumination light becomes a set value based on the corrected amount of received light and the first temperature; and control, when a temperature of at least one of the first temperature or the second temperature becomes equal to or higher than a predetermined temperature, driving of the light source so that the temperature of the at least one of the first temperature or the second temperature does not exceed the predetermined temperature.

2. The endoscope according to claim 1, wherein the controller is configured to correct, based on a difference between an amount of received light after the correction and the set value and the first temperature, a drive signal for driving the light source so that the difference decreases.

3. The endoscope according to claim 1, wherein the controller is configured to correct the amount of light received by the optical sensor using a first table for storing sensitivity data of the optical sensor corresponding to the second temperature.

4. The endoscope according to claim 1, wherein the controller is configured to correct the amount of light received by the optical sensor in consideration of a wavelength of the illumination light corresponding to the first temperature.

5. The endoscope according to claim 4, wherein the controller is configured to correct the amount of light received by the optical sensor using a second table for storing peak wavelength data of the illumination light corresponding to the first temperature, and a third table for storing sensitivity data corresponding to the second temperature and the peak wavelength.

6. The endoscope according to claim 1, wherein
the endoscope has an optical fiber for guiding the illumination light, and
the optical sensor is arranged in a vicinity of an incident end of the optical fiber.

7. The endoscope according to claim 1, wherein
the endoscope has an optical fiber for guiding the illumination light, and
the optical sensor is arranged in a vicinity of an emission end of the optical fiber.

8. The endoscope according to claim 1, wherein the optical sensor and the second temperature sensor are mounted on a circuit board sandwiching the circuit board.

9. The endoscope according to claim 1, wherein the light source and the optical sensor are provided in an operation portion of the endoscope or in a portion of the endoscope in a vicinity of the operation portion.

10. The endoscope according to claim 1, wherein
the endoscope includes a phosphor configured to convert a wavelength of a part of light emitted from the light source, and
the illumination light is mixed light of light emitted from the light source and wavelength-converted light.

11. An endoscope comprising:
the endoscope according to claim 1, and
an image processor comprising hardware, the image processor being configured to increase a luminance of the image when a temperature of at least one of the first temperature or the second temperature becomes equal to or higher than the predetermined temperature.

12. An endoscope comprising:
the endoscope according to claim 1, and
an image processor comprising hardware, the image processor being configured to adjust a color of the image using a second table for storing peak wavelength data of the illumination light corresponding to the first temperature and a fourth table for storing color coefficient data corresponding to the peak wavelength.

* * * * *